United States Patent

Kanda et al.

Patent Number: 5,380,843
Date of Patent: Jan. 10, 1995

[54] PROCESS FOR THE PREPARATION OF PHENYL (1,3,5-TRIAZIN-2-YL)CARBAMATES

[75] Inventors: Yoichi Kanda; Hideo Arabori, both of Iwaki, Japan

[73] Assignee: Kureha Kagaku Kogyo K.K., Tokyo, Japan

[21] Appl. No.: 63,594

[22] Filed: May 19, 1993

[30] Foreign Application Priority Data

Jun. 2, 1992 [JP] Japan ................... 4-165530

[51] Int. Cl.$^6$ ................... C07D 251/70; C07D 251/18; C07D 251/40; C07D 251/48
[52] U.S. Cl. ................... 544/197; 544/206; 544/208; 544/211
[58] Field of Search ................ 544/197, 206, 208, 211

[56] References Cited

FOREIGN PATENT DOCUMENTS

| | | |
|---|---|---|
| 0070802A2 | 1/1983 | European Pat. Off. |
| 0070804A2 | 1/1983 | European Pat. Off. |
| 0085028A2 | 8/1983 | European Pat. Off. |
| 0101670A2 | 2/1984 | European Pat. Off. |
| 0103543A2 | 3/1984 | European Pat. Off. |
| 0235449A1 | 9/1987 | European Pat. Off. |
| 0238070A2 | 9/1987 | European Pat. Off. |
| 60-139691 | 7/1985 | Japan . |
| 2112783A | 7/1983 | United Kingdom . |

Primary Examiner—John M. Ford
Attorney, Agent, or Firm—Lowe, Price, LeBlanc & Becker

[57] ABSTRACT

Phenyl (1,3,5-triazin-2-yl)carbamates of the formula (I):

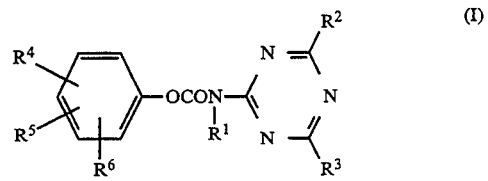

wherein $R^1$ is H, $C_1$–$C_4$ alkyl or $C_1$–$C_4$ alkoxy, $R^2$ and $R^3$ are independently H, halogen atom, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, $C_1$–$C_4$ haloalkylthio, $C_2$–$C_4$ alkoxyalkyl or $NR^7R^8$ ($R^7$, $R^8$: H or $C_1$–$C_4$ alkyl, independently), and $R^4$, $R^5$ and $R^6$ are independently H, halogen atom, $C_1$–$C_4$ alkyl or $C_1$–$C_4$ alkoxy, are prepared by reacting a 2-amino-1,3,5-triazine of the formula (II):

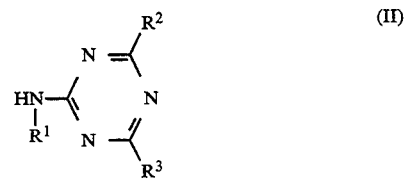

with a diphenyl carbonate of the formula (III):

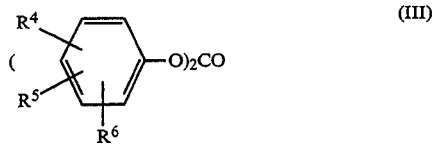

in the presence of an alkali metal hydride in an acrotic polar solvent. An parotic polar solvent mixture of the phenyl (1,3,5-triazin-2-yl)carbamate of the formula (I) and an alkali metal phenoxide is also disclosed.

3 Claims, No Drawings

PROCESS FOR THE PREPARATION OF PHENYL (1,3,5-TRIAZIN-2-YL)CARBAMATES

BACKGROUND OF THE INVENTION

This invention relates a process for the preparation of phenyl (1,3,5-triazin-2-yl)carbamates which are useful intermediates for producing of herbicidally active sulfonylurea compounds.

EP-A-85028 (corresponding to JP-A-58146572), EP-A-103543 (corresponding to JP-A-5973583), JP-A-60139691 and EP-A-238070 (corresponding to JP-A-6438091) disclose that phenyl (1,3,5-triazin-2-yl)carbamates and phenyl (pyrimidin-2-yl)carbamates are used as intermediates for producing of herbicidally active sulfonylurea compounds.

Preparations of phenyl (pyrimidin-2-yl)carbamates are relatively simple methods in a good yield.

However, simple synthesis method of phenyl (1,3,5-triazin-2-yl)carbamates is not reported.

(c.f. reference examples 53 and 57 in EP-A-238070)

SUMMARY OF THE INVENTION

An object of the present invention is to provide a process to prepare phenyl (1,3,5-triazin-2-yl)carbamates of the formula (I), which is simple and has a good yield.

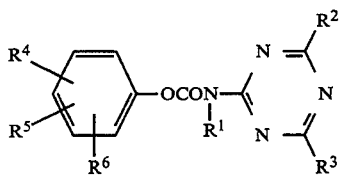

wherein
$R^1$ is hydrogen atom, $C_1$–$C_4$ alkyl or $C_1$–$C_4$ alkoxy
$R^2$ and $R^3$ are independently hydrogen atom, halogen atom, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, $C_1$–$C_4$ haloalkylthio, $C_2$–$C_4$ alkoxyalkyl or $NR^7R^8$
$R^7$ and $R^8$ are independently hydrogen atom or $C_1$–$C_4$ alkyl
$R^4$, $R^5$ and $R^6$ are independently hydrogen atom, halogen atom, $C_1$–$C_4$ alkyl or $C_1$–$C_4$ alkoxy Another object of the invention is to provide a resultant mixture reacting 2-amino-1,3,5-triazines of the formula (II)

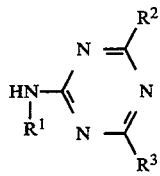

with diphenyl carbonates of the formula (III) in the presence of alkali metal hydrides in aprotic polar solvents, which contains phenyl (1,3,5-triazin-2-yl)carbamates of the formula (I) and alkali metal phenoxides of the formula (IV)

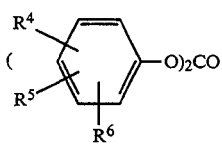

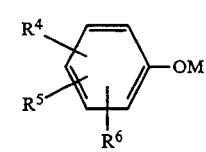

wherein $R^1$, $R^2$, $R^3$, $R^4$, $R^5$ and $R^6$ are as defined above and M is alkali metal atom.

DETAILED DESCRIPTION OF THE INVENTION

According to the present invention there is therefore provided a process for the preparation of phenyl (1,3,5-triazin-2-yl)carbamates of the formula (I)

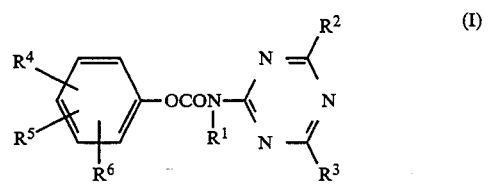

wherein
$R^1$ is hydrogen atom, $C_1$–$C_4$ alkyl or $C_1$–$C_4$ alkoxy
$R^2$ and $R^3$ are independently hydrogen atom, halogen atom, $C_1$–$C_4$ alkyl, $C_1$–$C_4$ alkoxy, $C_1$–$C_4$ alkylthio, $C_1$–$C_4$ haloalkyl, $C_1$–$C_4$ haloalkoxy, $C_1$–$C_4$ haloalkylthio, $C_2$–$C_4$ alkoxyalkyl or $NR^7R^8$
$R^7$ and $R^8$ are independently hydrogen atom or $C_1$–$R_4$ alkyl
$R^4$, $R^5$ and $R^6$ are independently hydrogen atom, halogen atom, $C_1$–$c_4$ alkyl or $C_1$–$C_4$ alkoxy which comprises reacting 2-amino-1,3,5-triazines of the formula (II)

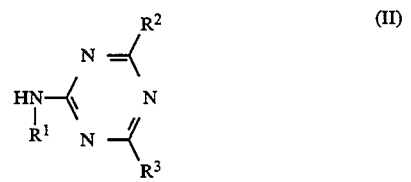

with diphenyl carbonates of the formula (III)

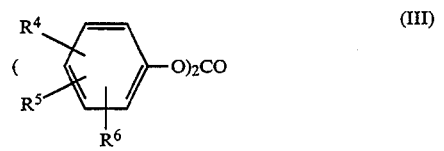

in the presence of alkali metal hydrides in aprotic polar solvents.

In a suitable process for the preparation of said phenyl (1,3,5-triazin-2-yl)carbamates, said 1,3,5-triazine derivatives are reacted with alkali metal hydrides and then with said diphenyl carbonates in aprotic polar solvents.

Halogen in the above definitions, and also as moiety of haloalkyl, haloalkoxy and haloalkylthio, is fluorine, chlorine, bromine arid iodine, with fluorine and chlorine being preferred.

Haloalkyl, haloalkoxy and haloalkylthio are substituted with one or more halogen atoms.

In suitable 2-amino-1,3,5-triazines of the formula (II), $R^1$ is hydrogen atom, $R^2$ and $R^3$ are independently $C_1$-$C_2$ alkyl, $C_1$-$C_2$ alkoxy, $C_1$-$C_2$ fluoroalkyl, $C_1$-$C_2$ fluoroalkoxy, $C_2$-$C_4$ alkoxyalkyl or $NR^7R^8$, $R^7$ and $R^8$ are independently hydrogen atom or $C_1$-$C_2$ alkyl.

Fluoroalkyl, fluoroalkoxy and fluoroalkylthio in the above definitions are substituted with one or more fluorine atoms.

In suitable diphenyl carbonates of the formula (III), $R^4$, $R^5$ and $R^6$ are independently hydrogen atom or methyl.

The process of the invention is illustrated by the following reaction scheme,

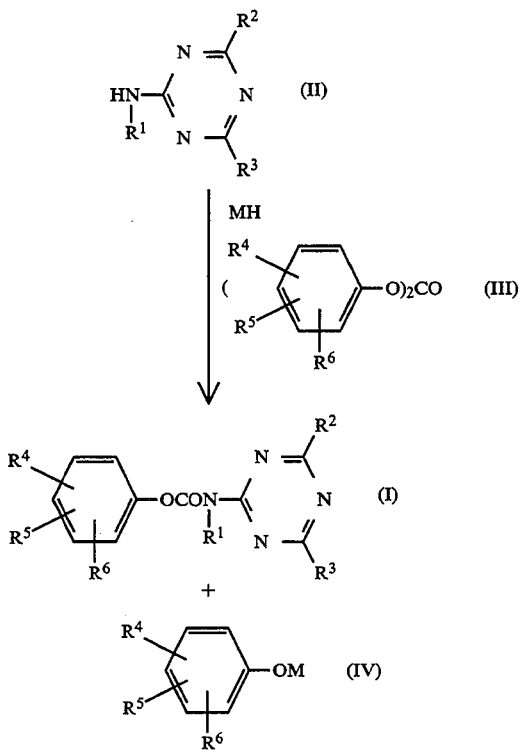

wherein $R^1$, $R^2$, $R^3$, $R^4$, $R^5$ and $R^6$ are as defined above and M is alkali metal atom.

A single aprotic polar solvent or a mixed solvent containing one or more aprotic polar solvents may be used in the invention.

An aprotic nonpolar solvent may be used as the other component of the mixed solvent, if it dose not give the bad effect to the reaction yield.

Suitable aprotic polar solvents exemplify N,N-dimethylacetamide, N-methylpyrrolidone and acetonitrile.

As suitable alkali metal hydrides, sodium hydride or potassium hydride may be exemplified.

The reaction is preferably carried out at a temperature from 0° to 40 ° C. to give phenyl (1,3,5-triazin-2-yl)carbamates of the formula (I) in good yields.

The reaction temperature may be out of the range from 0° to 40° C. if it needs for the reaction operation and dose not give the product in bat yields.

Reaction time is preferably 5–30 minutes after mixing 2-amino-1,3,5-triazines of the formula (II), alkali metal hydrides and diphenyl carbonates of the formula (III).

But, elongation of the reaction time is allowed in the extent without giving the bad effect to the reaction yield, if necessary for the reaction operation.

Alkali metal hydrides and diphenyl carbonates of the formula (III) are employed an equimolar amount per mole of 2-amino-1,3,5-triazines of the formula (II), respectively, to give the objective compound in good yields.

But, per mole of the most expensive starting compound, excesses of the other starting compounds may be used in the extent without giving the bad effect to the reaction yield.

The used amount of a reaction solvent is not restricted especially, since the object of the invention is satisfied that staring materials are mixed well in it.

The ratio or the sum of used starting materials (gr. weight) to used solvent (ml. volume) is preferably in the range of ⅓–1/10 (gr/ml).

In the case of isolating phenyl (1,3,5-triazine-2-yl)carbamates of the formula (I) from the resultant mixture of above reaction operation, the resultant mixture is poured into the iced-water containing 1.1–5 moles of hydrogen chloride per mole of used alkali metal hydride.

The precipitate is filtered off and washed with petroleum ether or hexane to give the product.

Of course, if necessary, recrystallization or column chromatography may be used for further purification process.

However, in the case of using phenyl (1,3,5-triazin-2-yl)carbamates of the formula (I) for the reagent of [(1,3,5-triazin-2-yl)amino]carbonylation at the nitrogen atom of a sulfonamide group, the aprotic polar solvent containing phenyl (1,3,5-triazin-2-yl)carbamates of the formula (I) and alkali metal phenoxides of the formula (IV) (corresponding to the above resultant reaction mixture) may be used without further adding base compounds.

Therefore, the use of She above resultant reaction mixture is of commercial interest on account of the advantages mentioned.

The invention is further illustrated by the following examples, in which 2-amino-4,6-dimethoxy-,1,3,5-triazine as 2-amino-1,3,5-triazines of the formula (II), diphenyl carbonate as diphenyl carbonates of the formula (III), sodium hydride as alkali metal hydrides, N,N-dimethylacetamide as aprotic polar solvents and methyl 2-(aminosulfonyl)benzoate as compounds having a sulfonamide group are used.

However, the present invention is not limited to the following examples so far as not coming over the essential features thereof.

EXAMPLE 1

The Preparation of phenyl (4,6-dimethoxy-1,3,5-triazin-2-yl)carbamate

Into 50 ml Erlenmeyer flask, were added 2-amino-4,6-dimethoxy-1,3,5-triazine 2.00 g (0.0128 mole) and dry N,N-dimethylacetamide 18 ml and stirred in the suspended condition.

To the suspended mixture, at the room temperature, was added 60% oily sodium hydride 0.51 g (0.0128 mole).

The reaction mixture was homogeneous after vigorous evolution of hydrogen gas.

A solution of diphenyl carbonate 2.74 g (0.0128 mole) and dry N,N-dimethylacetamide was subsequently added to the mixture under the water cooling during 10 minutes, and stirred for further 10 minutes.

The reaction mixture was poured into 20 ml iced water containing 1.4 ml hydrogen chloride (35% aq soln).

The precipitate was filtered off and wash with iced water and then petroleum ether.

After being air-dried, the product was obtained.

The obtained amount (yield of theory) and the physical property were showed hereinafter.

2.60 g (73.5% of theory)
mp. 141°–142° C.
IR (KBr,cm$^{-1}$) 3304, 1780, 1752, 1618, 1482 1390, 1360, 1290, 1192
NMR (CDCl$_3$, δ)
4.0(6H, s, OCH$_3\times$2)7.05–7.5(5H, m, Aromatic H) 8.28–8.7(1H, bs, NH)

EXAMPLE 2

The Use of the N,N-dimethylacetamide Mixture for [(1,3,5-triazin-2-yl)amino]carbonylation at the Nitrogen Atom of a Sulfonamide Group

[1]

Preparation of the N,N-dimethylacetamide mixture containing phenyl (4,6-dimethoxy-1,3,5-triazin-2-yl)carbamate and sodium phenoxide Into 50 ml Erlenmeyer flask, were added 2-amino-4,6-dimethoxy-1,3,5-triazine 1.00 g and dry N,N-dimethylacetamide 9 ml, and stirred in suspended condition.

To the suspended mixture, at the room temperature, was added 60% oily sodium hydride 0.26 g.

The reaction mixture was homogeneous after vigorous evolution of hydrogen gas.

A solution of diphenyl carbonate 1.37 g and dry N,N-dimethylacetamide 4.2 ml was subsequently added dropwise to the mixture under water cooling during 6 minutes.

Stirring was maintained for further 10 minutes to prepare the N,N-dimethylacetamide mixture containing phenyl (4,6-dimethoxy-1,3,5-triazin-2-yl)carbamate and sodium phenoxide.

[2]

Preparation of methyl 2-[[(4,6-dimethoxy-1,3,5-triazin-2-yl)aminocarbonyl]aminosulfo nyl]benzoate The N,N-dimethylacetamide mixture in 50 ml Erlenmeyer flask, obtained in [1], was stirred under iced water cooling.

To the mixture, was added dropwise a solution of methyl 2-(aminosulfonyl)benzoate 1.25 g and N,N-dimethylacetamide 3 ml for 5 minutes.

The mixture was stirred for further 1.5 hours.

The mixture was subsequently poured into 130 ml iced water containing 0.7 ml hydrogen chloride (35% aq soln).

A white precipitate was filtered off and washed with iced water and then petroleum ether, and air-dried to give the product.

The obtained amount (yield of theory) and the physical property were showed hereinafter.

1.90 g (82.2% of theory)
purity by HPLC 97.8%
mp. 171°–173° C.
IR (KBr,cm$^{-1}$) 3320, 1742, 1608, 1494, 1388, 1292
NMR (d$_6$-DMSO, δ)
3.8(3H, s)3.95(6H, s)7.26–8.3(5H, m)10.9(1H, bs)

What is claimed is:

1. A process for the preparation of a phenyl (1,3,5-triazin-2-yl)carbamate of the formula (I):

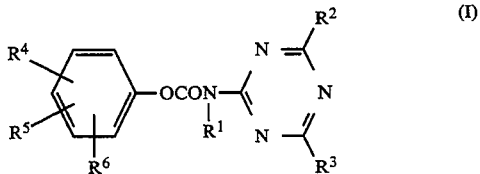

wherein
R$^1$ is hydrogen atom, C$_1$–C$_4$ alkyl or C$_1$–C$_4$ alkoxy,
R$^2$ and R$^3$ are independently hydrogen atom, halogen atom, C$_1$–C$_4$ alkyl, C$_1$–C$_4$ alkoxy, C$_1$–C$_4$ alkylthio, C$_1$–C$_4$ haloalkyl, C$_1$–C$_4$ haloalkoxy, C$_1$–C$_4$ haloalkylthio, C$_2$–C$_4$ alkoxyalkyl or NR$^7$R$^8$,
R$^7$ and R$^8$ are independently hydrogen atom or C$_1$–C$_4$ alkyl,
R$^4$, R$^5$ and R$^6$ are independently hydrogen atom, halogen atom, C$_1$–C$_4$ alkyl or C$_1$–C$_4$ alkoxy, which process comprises:
reacting a 2-amino-1,3,5-triazine of the formula (II):

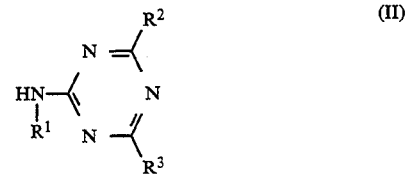

wherein R$^1$, R$^2$ and R$^3$ are as recited for formula I with a diphenyl carbonate of the formula (III):

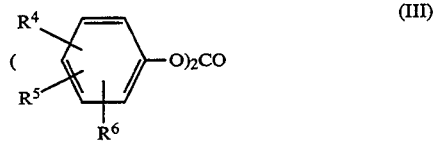

wherein R$^4$, R$^5$ and R$^6$ are as recited in formula I, in the presence of an alkali metal hydride in an aprotic polar solvent.

2. A process according to claim 1, wherein a 2-amino-1,3,5-triazine of the formula (II) is reacted with said alkali metal hydride and then with a diphenyl carbonate of the formula (III) in said aprotic polar solvent.

3. A process according to claim 1 or 2, wherein said aprotic polar solvent is N,N-dimethyl-acetamide, N-methylpyrrolidone or acetonitrile.

* * * * *